(12) United States Patent
Saeed et al.

(10) Patent No.: US 7,182,756 B2
(45) Date of Patent: Feb. 27, 2007

(54) DEVICE FOR DIRECTING A WIRE GUIDE

(75) Inventors: Zahid Saeed, Cincinnati, OH (US); Vihar C. Surti, Winston-Salem, NC (US)

(73) Assignee: Wilson-Cook Medical, Inc., Winston-Salem, NC (US)

( * ) Notice: Subject to any disclaimer, the term of this patent is extended or adjusted under 35 U.S.C. 154(b) by 342 days.

(21) Appl. No.: 10/447,980

(22) Filed: May 29, 2003

(65) Prior Publication Data

US 2004/0073108 A1  Apr. 15, 2004

Related U.S. Application Data

(60) Provisional application No. 60/384,055, filed on May 29, 2002.

(51) Int. Cl.
*A61M 31/00* (2006.01)

(52) U.S. Cl. ............... 604/509; 604/510; 604/104; 604/96.01; 604/264

(58) Field of Classification Search ............ 604/194, 604/96.01, 264, 523, 528, 164.13
See application file for complete search history.

(56) References Cited

U.S. PATENT DOCUMENTS

| 4,774,949 | A | * | 10/1988 | Fogarty | 606/108 |
|---|---|---|---|---|---|
| 5,342,297 | A | | 8/1994 | Jang | |
| 5,413,581 | A | | 5/1995 | Goy | |
| 5,776,101 | A | * | 7/1998 | Goy | 604/104 |
| 6,090,096 | A | | 7/2000 | St. Goar et al. | |
| 6,645,195 | B1 | * | 11/2003 | Bhat et al. | 604/528 |

* cited by examiner

*Primary Examiner*—Nicholas D. Lucchesi
*Assistant Examiner*—Aamer Syed Ahmed
(74) *Attorney, Agent, or Firm*—Brinks Hofer Gilson & Lione

(57) ABSTRACT

A device for directing a wire guide into a bodily passageway such as a branch of the biliary tree or other difficult to access bodily passageway. The device includes a member, such as an inflatable balloon or a self-expanding basket, for obstructing a first passage. Once the balloon is inflated, or the basket expanded, the wire guide can be reliably directed or deflected into a preferred adjacent passageway in order to cannulate the preferred adjacent passageway. A procedure for cannulating a preferred passageway by obstructing a passageway in the natural flow-path of a wire guide is also provided.

17 Claims, 4 Drawing Sheets

# DEVICE FOR DIRECTING A WIRE GUIDE

RELATED APPLICATIONS

This claims the benefit of U.S. Provisional Application Ser. No. 60/384,055, filed May 29, 2002, entitled "Device For Directing A Wire Guide."

TECHNICAL FIELDS

This invention relates to medical devices, and more particularly to a flexible elongate member having means to direct a wire guide through a bodily passageway.

BACKGROUND OF THE INVENTION

Navigating a wire guide or catheter through a body passage can be especially problematic when attempting to negotiate a branching pathway, such as a bifurcated duct or vessel. Although adding steerability to a medical device is possible, it usually adds to the diameter of the device (a serious disadvantage in endoscopy) and may not result in a device having the desired characteristics. Most wire guides lack a satisfactory means to guide them in a particular direction, especially a direction that is against the natural pathway that the device wants to take. An example of an area of the body where this poses a problem is the biliary tree, where wire guides are often introduced prior to ERCP and other procedures involving the gall bladder, pancreas, liver, and associated ducts. The biliary tree includes bifurcations at the junction of the biliary and pancreatic ducts, as well as the right and left hepatic ducts. Using fluoroscopy or a cholangioscope, it is sometimes possible to successfully navigate the wire guide or device into the desired branch of the bifurcation; however, some anatomies can make that extremely difficult.

Adding steerability to a small-diameter wire guide like those used in endoscopy is generally not an option. One solution is to occlude the non-target branch of the bifurcation by inflating a balloon just past the junction. The balloon can be used to deflect a wire guide which is separately introduced through a different lumen of the scope, thereby directing it into the desired duct. While this method has been used successfully, a certain amount of trial and error is often required, primarily due to difficulties in visualizing the ducts and the lack of directional control over the wire guide. What is needed is a device that is configured such that the wire guide can be aligned with the occlusive means such that it reliably deflects it in a predictable manner and direction to successfully cannulate a particular branch of a bifurcated duct or vessel.

SUMMARY OF THE INVENTION

The foregoing problems are solved and a technical advance is achieved in an illustrative apparatus comprising an elongate member, such as a endoscopic balloon catheter, that includes an obstructive member (e.g., an inflatable or expandable member) having a first configuration and a second expanded configuration sized and configured for blocking a first bodily passageway, such as one branch of a bifurcated duct, blood vessel, or the bronchial tree. The apparatus further includes a first lumen having an external opening that is situated and aligned such that an elongated medical device, such as a wire guide, is advanced out of the external opening, whereby it contacts the obstructive member in the expanded configuration and is deflected away from the first bodily passageway and into the second bodily passageway (e.g., the opposite branch of the bifurcation) in a generally predictable manner.

In a first aspect of the present invention, the elongate member comprises a balloon catheter in which the obstructive member comprises a balloon that is inflated to block one branch of a bifurcated passageway. A wire guide is advanced through a first lumen of the balloon catheter until it exits via an external opening, such as a scive formed in the tubing proximal to the balloon. The external opening is aligned and configured such that the wire guide deflects out of the lumen where it contacts the inflated balloon and is further deflected away from the blocked first bodily passageway of the bifurcation (the natural or "preferred" pathway that the wire guide would otherwise travel) and into the open, second bodily passageway of the bifurcation. In the illustrative embodiment, a plug situated within the first lumen beyond the scive, forces deflection of the wire guide out of the lumen and external opening. The balloon catheter includes a second lumen for accommodating a wire guide that is extendable from the distal tip of the catheter to access the first bodily passageway, and a third lumen for inflation of the balloon.

In a second aspect of the invention, the apparatus includes an outer sheath with at least two lumens, the first lumen coaxially housing an elongate member, such as a balloon catheter, and a second lumen for a wire guide. The balloon catheter is advanced from the distal end of the outer member and inflated to block the first bodily passageway. The wire guide is advanced from the external opening located at the distal end of the outer sheath, the opening being situated such that the advancing wire guide deflects off of the surface of the expanded balloon and toward the second bodily passageway.

In a third aspect of the invention, the obstructive member of the apparatus comprises a self-expanding member, such as a stainless steel or nitinol basket that includes a surface configuration of sufficient density, such as fabric or metallic mesh, that allows a wire guide to deflect off of the obstructive member. Alternatively, the obstructive member may be made expandable in another manner, such as longitudinal compression or some other well-known means.

BRIEF DESCRIPTION OF THE DRAWINGS

Embodiments of the present invention will now be described by way of example with reference to the accompanying drawings, in which.

DETAILED DESCRIPTION

Figure 1:
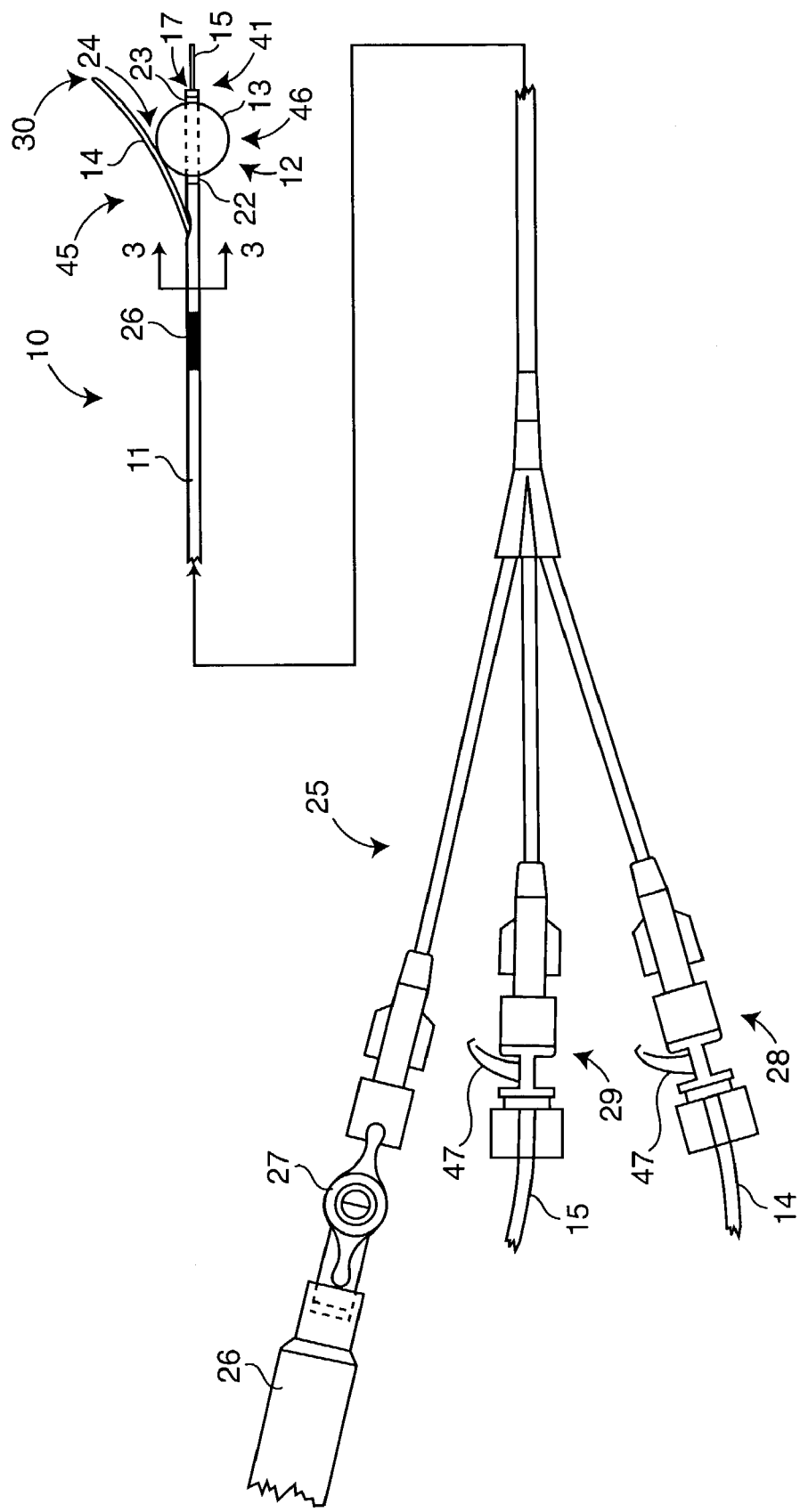
FIG. 1 depicts a side view of the illustrative embodiment of the present invention.
Figure 4:
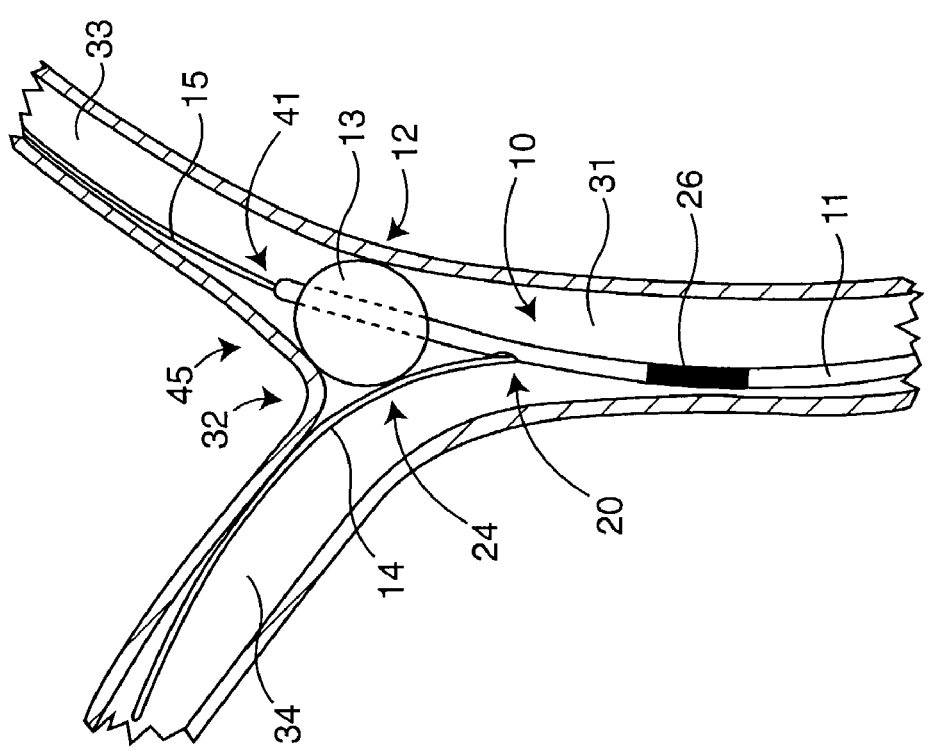
FIG. 4 depicts the embodiment of FIG. 1 in situ.

FIG. 1 depicts an illustrative embodiment of the present invention. In particular, an apparatus 10 is provided for directing an elongate medical device 14, such as a wire guide or catheter, into a particular bodily passageway, such as a branch of a bifurcated duct, common duct, or vessel 31 (which is depicted in FIGS. 4 and 6). The apparatus comprises an elongate member 11, such as a catheter, that includes an obstructive member 12 affixed about the distal portion 46 thereof. The obstructive member 12 is remotely expandable or inflatable from a first configuration 44 (e.g., FIG. 5) and size, such as one having a low profile that enables the elongate member to be navigated within the patient, to a second, larger configuration 45 (e.g., FIG. 4) and size for at least partially occluding a particular bodily passageway into which the operator does not wish the elongate medical device 14 to enter. The portion of the apparatus 10 illustrated in FIG. 2 includes a first lumen 16 sized to accommodate the elongate medical device 14 which is then advanced out of an external opening 19, such as a scive 20 in the apparatus that communicates with the first lumen 16. The external opening 19 is situated or aligned relative to the obstructive member 12 such that as the elongate medical device 14 is advanced out of the external opening 19, it comes into contact with the expanded obstructive member 12 (i.e., when in the second configuration 45) and is deflected in a particular direction. For example, the medical device 14 is deflected from its natural pathway and away from the first bodily passageway 33 (see FIG. 4), and toward the intended second bodily passageway 34, which typically is the opposite branch emanating from the common duct or vessel 31 through which the apparatus is being navigated.

Figure 3:
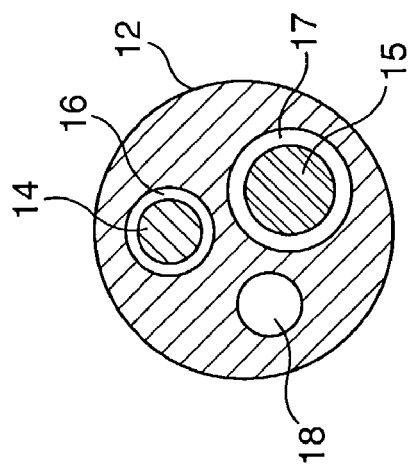
FIG. 3 depicts a cross-sectional view taken along line 3—3 of FIG. 1.

A first embodiment of the present invention is depicted in FIGS. 1–4 for use in the biliary tree in which the elongate member 11 of the apparatus 10 comprises a endoscopic balloon catheter and the obstructive member 12 comprises a balloon, typically made of a compliant material such as latex or silicone. The shaft portion of the elongate member 11, which is made of a biocompatible polymer, such as PEBAX® resin (ATOFINA Chemicals, Inc., Philadelphia, Pa.) or some other suitable material, includes three passageways or lumens 16, 17, 18 extending therethrough (FIG. 3). The first lumen 16 is sized to accommodate a standard wire guide 14, such as a 0.025" METRO™ Wire Guide (Wilson-Cook Medical). In the illustrative embodiment, the second lumen 17 is sized to accept a second wire guide 15, such as a 0.035" METRO™ Wire Guide. The second lumen 17 extends the length of the catheter 11. At the distal end of lumen 17, catheter 11 includes a distal opening 41 from which the second wire guide 15 may exit to access the blocked passageway or provide access so that the apparatus 10 can track over the second wire guide 15 if already in place. The third lumen 18 has a diameter of approximately 0.019" and communicates with an inflation port 38 located inside the balloon 13. The three lumens 16, 17, 18 each are accessible via hub connectors 27, 28, 29, respectively, which comprise the proximal hub assembly 25. The illustrative hub connector 27 that feeds the inflation lumen 18 and balloon 13, includes a stopcock and a luer fitting for attaching to an inflation device 26, such as a syringe. The hub connectors 28, 29 for the first 14 and second 15 wire guides, respectively, each include a Touhy-Borst adaptor and side-arm port 47 for infusion of fluids around the wire guide 14, 15, if necessary.

Figure 2:
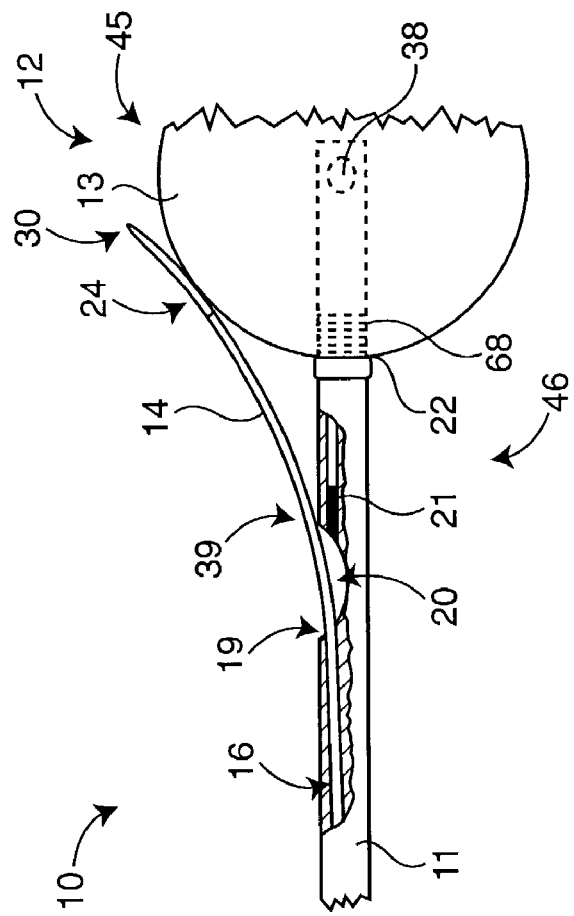
FIG. 2 depicts a partially sectioned detail view of the embodiment of FIG. 1.

Referring now to FIG. 2, the catheter lumen 16 for accommodating the wire guide 14 of the illustrative first embodiment includes an external opening 19 that comprises a scive 20 formed in the side of the tubing at a location proximal to the balloon 13. A plug 21, such as a metal or plastic insert or other permanent obstruction such as a cured adhesive material, helps to deflect and force the advancing wire guide out of lumen 16 via the scive 20, which is configured to guide the wire guide 14 toward the balloon 13. In the embodiment shown, the proximal edge of the balloon 13 is located about 1–2 cm from the external opening 19. The balloon 13 is affixed to the shaft of the catheter using a standard bond means 68, such as an adhesive and a wrapping. Additionally, radiopaque metal bands 22, 23 are placed to identify the proximal and distal ends of the balloon. Another radiopaque maker 26, such as a band of radiopaque ink, is also conveniently included proximal to the external opening 19. The typical diameter of the illustrative balloon 13 intended for biliary use, is approximately 10–15 mm when fully inflated. The point of contact 24 at which the tip of the wire guide 14 first abuts the balloon 13, when the balloon is in the inflated configuration 45, is somewhat variable, depending on the shape and size of the balloon when lodged within the first passageway; however, it is generally located as a point along the balloon's proximal or rearward portion such that when the balloon 13 is properly inflated (i.e., not overinflated or underinflated), the advancing wire guide 14 glances off of the balloon and is directed laterally (i.e., further away from the longitudinal axis of the catheter 11). It should be noted that an overinflated balloon may assume a squarish shape that may not permit the wire guide 14 to properly deflect in the desired manner.

FIG. 4 depicts the illustrative endoscopic biliary catheter being used to direct a wire guide away from the obstructed first bodily passageway 33, such as the right hepatic duct, and into a second bodily passageway 34, such as the left hepatic duct. In this particular instance, the physician may have attempted to cannulate the left (second) branch 34, but was unable to do so because the wire guide 14 tended to follow a natural pathway into the right (first) branch 33 instead. To address this problem, the apparatus 10 is advanced just pass the point of bifurcation 32 into the first branch 33, which in the illustrative situation, has been cannulated by the second wire guide 15. The balloon 13 is then inflated such that it generally obstructs the entrance to the first or right branch 33. The wire guide 14 is then manually advanced through the catheter 11 and out of the scive 20, where it contacts the balloon 13 along the rearward portion 24 thereof, thereby deflecting the wire guide 14 away from the balloon 13 and toward, and ultimately into, the second or left branch 34. Once successful cannulation has occurred, balloon 13 can be deflated and the catheter portion 11 of the apparatus withdrawn, leaving the wire guide 14 (or both wire guides 14, 15) in place.

Figure 5:
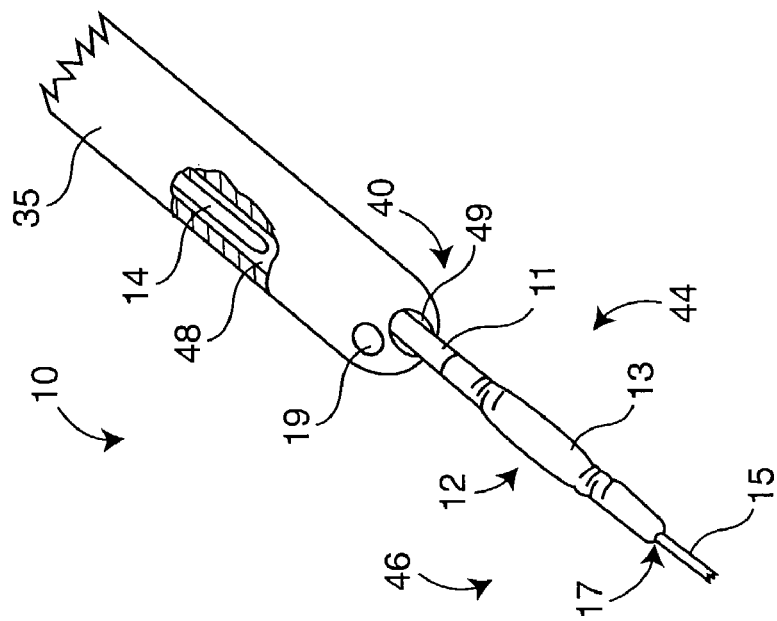
FIG. 5 depicts a pictorial view of an alternative embodiment of the present invention that includes an outer member.
Figure 6:
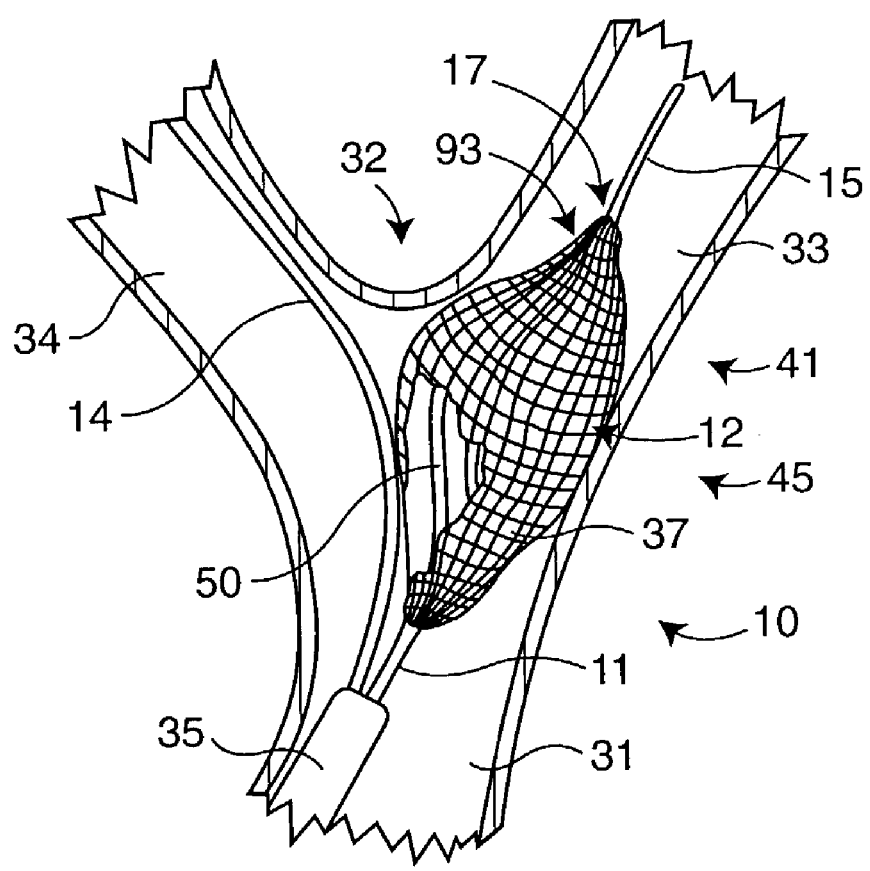
FIG. 6 depicts an alternative embodiment of the present invention in situ, wherein the obstructive member comprises an expandable member.

A second embodiment of the present invention is depicted in FIG. 5 in which the apparatus 10 further includes an outer member 35 having a first passageway 48 for receiving the first wire guide 14 and a second passageway 49 for accommodating the elongate member 11, which in the illustrative embodiment, comprises a balloon catheter. The external opening 19, through which the wire guide 14 exits to contact and deflect off of the balloon 13 (shown here in the first or deflated configuration 44), is located at the distal end 40 of outer member 35, rather than at an intermediate point along the elongate member 11 as in the embodiment of FIG. 1. The second passageway 49 for the balloon catheter 11 and the first passageway 48 for the wire guide 14 are aligned with one another such that the wire guide 14 contacts the balloon 13 at a location 24 that enables the wire guide to be redirected in a manner similar to that depicted for the embodiment of FIG. 1. In the illustrative embodiment of FIG. 5, the elongate member includes lumens for inflating the balloon 13 and accommodating a second wire guide 15, but lacks the third lumen for receiving the first wire guide 14, which instead, is housed within the outer member 35.

A third embodiment of the present invention is depicted in FIG. 6, in which the obstructive member 12 comprises an expandable member such as expandable basket 93. In this embodiment, a self-expanding wire basket is mounted on an elongate member 11 comprising a flexible braided sheath, nitinol shaft, or the like to which an expandable basket 93 may be affixed. The wire members 50 of the expandable basket 93 are typically made of spring stainless steel or nitinol, such that they resiliently assume the expanded configuration 45 upon being advanced from the constraining outer member 35. The expandable basket 93 preferably includes a mesh covering 37, preferably made of a tight-woven and durable material, such as nylon, polyethylene terepthalate, etc. such that the wire guide 14 will deflect off of, rather than penetrate the fabric. It is possible, however, to construct a basket with a sufficient density of wire members 50 to accomplish the same function. In a related embodiment, the wire members 50 of the expandable member 93 could be eliminated and the mesh covering 37 comprise a material with shape memory, such as fine nitinol wire, so that it assumes the expanded configuration 45 with sufficient rigidity to form an effective obstructive member 12 for deflecting the wire guide 14. The illustrative embodiment optionally includes a lumen 17 for receiving a second wire guide 15. It should be noted that it is also within the scope of the invention for the expandable member 93 to be manually expandable, such as a basket that must be axially manipulated (i.e., longitudinally compressed) in order to expand the device, rather than the device being resiliently self-expanding.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. Certainly, one skilled in the medical arts would be able to conceive of a wide variety of obstructive member and elongate member configurations and successful combinations thereof. The selection of these and other details of construction are believed to be well within the ability of one of even rudimental skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in *The New Shorter Oxford English Dictionary*, 1993 edition. All technical terms shall take on their customary meaning as established by the appropriate technical discipline utilized by those normally skilled in that particular art area. All medical terms shall take their meaning as defined by *Stedman's Medical Dictionary*, 27th edition.

What is claimed is:

1. A medical device for directing an elongate member, comprising:

an elongate sheath comprising a proximal end, a distal end and a longitudinal axis extending therebetween;

an expandable obstruction member operatively connected to the elongate sheath;

a first passageway extending along the longitudinal axis from the proximal end to the obstruction member;

a second passageway extending along the longitudinal axis from the proximal end to a portion proximal to the obstruction member, the second passageway terminating at an exit port, the exit port being proximal to the obstruction member; and an elongate member slidable within the second passageway, the elongate member comprising a first portion disposed within the second passageway and a second portion extending through the exit port, the second portion of the elongate member contacting a surface of the obstruction member in a deflected configuration, wherein the second portion is deflected by the surface in a direction away from the longitudinal axis.

2. The medical device of claim 1, wherein the obstruction member is inflatable.

3. The medical device of claim 2, wherein the obstruction member is an inflatable balloon.

4. The medical device of claim 1, further comprising:

a third passageway extending along the longitudinal axis from the proximal end to the distal end, the third passageway terminating at an exit port; and a second elongate member axially slidable within the third passageway.

5. The medical device of claim 4, further comprising a hub operably connected to the proximal end.

6. The medical device of claim 5 wherein the hub comprises a first access port corresponding with the first passageway, a second access port corresponding with the second passageway, and a third access port corresponding with the third passageway.

7. The medical device of claim 6, further comprising a fluid control element operably connected to the first access port, and an inflation device operably connected to the fluid control element.

8. The medical device of claim 7, wherein the second access port comprises a side-arm port for infusion of fluid through the second passageway and the third access port comprises a side-arm port for infusion of fluid through the third passageway.

9. The medical device of claim 8, further comprising a plurality of radiopaque markers connected to the elongate sheath.

10. The medical device of claim 1, further comprising an internal deflecting member located within the second passageway, wherein the internal deflecting member is configured to deflect the elongate member through the exit port.

11. The medical device of claim 1, wherein the elongate member engages a rearward portion of the obstruction member.

12. The medical device of claim 1, wherein the obstruction member is disposed in a first body lumen passageway and a distal end of the elongate member is disposed in a second body lumen passageway adjacent the first body lumen passageway.

13. The medical device of claim 1, wherein the elongate member is a wire guide.

14. The medical device of claim 1, wherein the exit port is a scive configured to deflect the elongate member away from the longitudinal axis.

15. A method of directing a wire guide, the method comprising the steps of:

a) providing a medical device comprising:

an elongate sheath comprising a proximal end, a distal end and a longitudinal axis extending therebetween;

an obstruction member, the obstruction member being operatively connected to the elongate sheath;

a first passageway extending along the longitudinal axis from the proximal end to the obstruction member;

a second passageway extending along the longitudinal axis from the proximal end to a portion proximal to the obstruction member, the second passageway terminating at an exit port proximal to the obstruction member; and an elongate member slidable within the second passageway, wherein the obstruction member is configured to deflect the elongate member toward a desired direction away from the longitudinal axis;

b) inserting the elongate sheath into a branching body lumen having a first branch and a second branch adjacent to the first branch;

c) advancing a portion of the elongate sheath into the first branch, thereby positioning the obstruction member partially within the first branch;

d) expanding the obstruction member within the first branch, thereby obstructing entry into the first branch;

e) advancing the elongate member distally through the exit port;

f) deflecting the elongate member away from the longitudinal axis by contacting a surface of the obstruction member; and g) cannulating the second branch with the elongate member.

16. The method of claim 15, further comprising the steps of:

h) collapsing the obstruction member; and i) withdrawing the elongate sheath from the body lumen while maintaining the elongate member within the second branch.

17. A method of accessing a desired passageway branching from a body lumen, the method comprising the steps of:

a) providing a medical device comprising a wire guide, and a catheter having an inflatable balloon configured to deflect the wire guide;

b) inserting a portion of the catheter into a first branch of the body lumen;

c) inflating the balloon within the first branch, thereby obstructing the first branch;

d) advancing the wire guide through the body lumen and through an exit port proximal to the balloon, contacting the balloon with a portion of the wire guide and deflecting the wire guide away from the longitudinal axis; and e) advancing the wire guide into the desired passageway.

* * * * *